(12) United States Patent
Parkhurst et al.

(10) Patent No.: US 6,248,518 B1
(45) Date of Patent: *Jun. 19, 2001

(54) METHOD FOR DETECTING POINT MUTATIONS IN DNA UTILIZING FLUORESCENCE ENERGY TRANSFER

(75) Inventors: Lawrence J. Parkhurst; Kay M. Parkhurst; Lyle Middendorf, all of Lincoln, NE (US)

(73) Assignee: Board of Regents of University of Nebraska, Lincoln, NE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/958,809

(22) Filed: Oct. 22, 1997

Related U.S. Application Data

(60) Provisional application No. 60/029,775, filed on Oct. 29, 1996.

(51) Int. Cl.[7] .............................. C12Q 1/68; C12P 19/34; C07H 19/00; C07H 21/00
(52) U.S. Cl. ............................ 435/6; 435/5; 435/91.1; 536/22.1; 536/23.1; 536/24.3; 536/25.321
(58) Field of Search .................... 435/5, 6, 91.1; 536/22.1, 23.1, 24.3, 25.32

(56) References Cited

U.S. PATENT DOCUMENTS

| | | | |
|---|---|---|---|
| 4,871,838 | 10/1989 | Bos et al. | 536/27 |
| 4,996,143 * | 2/1991 | Heller et al. | 435/6 |
| 5,348,853 | 9/1994 | Wang et al. | 435/6 |
| 5,538,848 | 7/1996 | Livak et al. | 435/5 |
| 5,591,578 | 1/1997 | Meade et al. | 435/6 |
| 5,691,146 | 11/1997 | Mayrand | 435/6 |
| 5,723,591 | 3/1998 | Livak et al. | 536/22.1 |
| 5,780,233 | 7/1998 | Guo et al. | 435/6 |
| 5,866,336 | 2/1999 | Nazarenko et al. | 435/6 |
| 5,876,930 | 3/1999 | Livak et al. | 435/6 |

OTHER PUBLICATIONS

Hames et al. "Nucleic acid hybridization, a practical approach" IRL press, pp. 65, and 81, 1985.*

Sanjay Tyagi and Fred Russell Kramer, "Molecular Beacons: Probes that Fluoresce upon Hybridization," *Nature Biotechnology*, vol. 14, Mar. 1996, pp. 303–308.

(List continued on next page.)

*Primary Examiner*—Jezia Riley
(74) *Attorney, Agent, or Firm*—Shook, Hardy & Bacon L.L.P.

(57) ABSTRACT

A method for detecting point mutations in DNA using a fluorescently labeled oligomeric probe and Forster resonance energy transfer (FRET) is disclosed. The selected probe is initially labeled at each end with a fluorescence dye, which act together as a donor/acceptor pair for FRET. The fluorescence emission from the dyes changes dramatically from the duplex stage, wherein the probe is hybridized to the complementary strand of DNA, to the single strand stage, when the probe is melted to become detached from the DNA. The change in fluorescence is caused by the dyes coming into closer proximity after melting occurs and the probe becomes detached from the DNA strand. The change in fluorescence emission as a function of temperature is used to calculate the melting temperature of the complex or $T_m$. In the case where there is a base mismatch between the probe and the DNA strand, indicating a point mutation, the $T_m$ has been found to be significantly lower than the $T_m$ for a perfectly match probe\strand duplex. The present invention allows for the detection of the existence and magnitude of $T_m$, which allows for the quick and accurate detection of a point mutation in the DNA strand and, in some applications, the determination of the approximate location of the mutation within the sequence.

17 Claims, 4 Drawing Sheets

OTHER PUBLICATIONS

"DYEnamic energy transfer primers," Amersham Life Science, 1996.

"Thermo Sequenase Dyenamic ET Primers," Reader Enquiry No. 269, Amersham Life Science, 1996.

"Cassette Labeling for Facile Construction of Energy Transfer Fluorescent Primers," Jingyue Ju et al., Nucleic Acids Res. 1996, vol. 24, No. 6.

"New Products for Bioresearch," Circle Reader Service No. 207, vol. 21, No. 1 (1996).

"Energy Transfer Primers: A New Fluorescence Labeling Paradigm for DNA Sequencing and Analysis," J. Ju, et al., Nature Medicine, vol. 2, No. 2, pp. 246–249 (1996).

"Fluorescence Energy Transfer Dye–Labeled Primers for DNA Sequencing and Analysis,"J. Ju, et al., Proc. Natl. Acad. Sci. USA, vol. 92, pp. 4347–4351 (1995).

"Rapid Sizing of Short Tandem Repeat Alleles Using VCapillary Array Electrophoresis and Energy–Transfer Fluorescent Primers," Y. Wang et al., Analytical Chemistry, Vo. 67, No. 7, 1197–1203 (1995).

"Electrophoretically Uniform Fluorescent Dyes for Automated DNA Sequencing," M. Metzker et al., Science, vol. 271, 1420–1422 (1996).

"Dyes Identified for Automated DNA Sequencing," Biophotonics International, 34–35 (May/Jun. 1996).

"New Beacons Serve as Superior Fluorescent Probes," Biophotonics International, pp. 56–57 (May/Jun. 1996).

Page 5 from New Product Review, "TaqMan™ LS–50B PCR Detection System"and "Capillary Electrophoresis." 1995.

Brochure of Perkin Elmer, Applied Biosystems Div., ABI PRISM™ 7700 Sequence Detection System (1995).

Brochure of Perkin Elmer, Applied Biosystems Div., ABI PRISM™ 7700 Sequence Detection System (1996).

Brochure of Perkin Elmer, Applied Biosystems Div., "Quantitation of DNA/RNA Using Real–Time PCR Detection," Dr. K. Livak, 1–8 (1996).

"Quantitative PCR by Real Time Detection," T.M. Woudenberg and J. Stevens, Perkin Elmer, Applied Biosystems, Div., SPIE vol. 2680, 306–314 (1996).

"Real Time Quantitative PCR," C. Heid, et al., Genome Research, 986–994 (1996).

"Towards Fully Automated Genome–Wide Polymorphism Screening," Nature Genetics, vol. 9, 341—341 (Apr. 1995).

"Oligonucleotides with Fluorescent Dyes at Opposite Ends Provide a Quenched Probe System Useful for Detecting PCR Product and Nucleic Acid Hybridization," K. Livak, et al., PCR Methods and Applications, 357, 359, 361 (1995).

AcuGen Systems Research Products Price List 1994, by Biotronics Technologies Corp., 4 pages.

Review Paper: "Detection of Point Mutations in DNA by Fluorescence Energy Transfer," K.M. Parkhurst and L.J. Parkhurst, Journal of Biomedical Optics, vol. 1, No. 4, 435 441 (Oct. 1996).

Nature Biotechnology, vol. 14, p. 264 (Mar. 1996), "Lighting Up Hybridization," Charles R. Cantor.

Nature Biotechnology, vol. 14, 303–308 (Mar. 1996), "Molecular Beacons Probes that Fluoresce Upon Hybridization," S. Tyagi and F.R. Kramer.

Technical Abstract Digest, Bios '97, International Symposium on Biomedical Optics, p. 232 (Feb. 1997), "Detection of Nucleic Acids Using Fluorescence Energy Transfer and G–Quartet Probes," J.B. Pitner et al.

Cardullo et al. Detection of nucleic acid hybridization by nonradiative fluorescence resonance energy transfer. Proceedings of the National Academy of Sciences, USA. Dec. 1988, vol. 85, No. 23, pp. 8790–8794.

Uchiyama et al. Detection of Undegraded Oligonucleotides in Vivo by Fluorescence Resonance Energy Transfer. The Journal of Biological Chemistry. Jan. 1996, vol. 271, No. 1, pp. 380–384.

Iltia et al. Detection of a Point Mutation Using Short Oligonucleotide Probes in Allele–Specific Hybridization. BioTechniques. Sep. 1994, vol. 17, No. 3, pp. 566–573.

Pennisi, E., "Sifting Through and Making Sense of Genome Sequences," Science, vol. 280, Jun. 12, 1998, pp. 1692–1693.

Ota, N., et al., "Determination of Interactions Between Structured Nucleic Acids by Fluorescence Resonance Energy Transfer (FRET): Selection of Target Sites for Functional Nucleic Acids," Nucl. Acids. Res., vol. 26, No. 3, 1998, pp. 735–743.

Parkhurst, K.M., et al., "Detection of Point Mutations in DNA By Fluorescence Energy Transfer," J. Biomed. Optics, vol. 1, No. 4, Oct. 1996, pp. 435–441.

Germer, S., et al., Single–Tube Genotyping Without Oligonucleotide Probes, Genome Research, vol. 9, 1999, pp. 72–78.

Hodgson, J., Shrinking DNA Diagnostics to Fill the Markets of the Future, Nature Biotech., vol. 16, Aug. 1998, pp. 725–727.

"Thermo BioAnalysis Introduces Two Products for DNA Research," PRNewswire, May 20, 1999.

Howell, W.M., et al., "Dynamic Allele–Specific Hybridization," Nature Biotech., vol. 17, Jan. 1999, pp. 87–88.

"Hybaid Limited Partners Interactiva GMBH in Emerging Biochip Market," Hybaid News Release, Dec. 8, 1999.

P.R. Langer, A.A. Waldrop, and D.C. Ward, "Enzymatic Synthesis of Biotin–Labeled Plynucleotides: Novel Nucleic Acid Affinity Probes," Proc. Natl. Acad. Sci., U.S.A. 78, 6633–6637 (1981).

P. Tchen, R.P.P. Ruchs, E. Sage, and M. Leng, "Chemically Modified Nucleic Acids as Immuno–Detectable Probes in Hybridization Experiments," Proc. Natl. Acad. Sci., US.A. 81, 3466–3470 (1984).

S. Tomlinson, A. Lyga, E. Huguenel, and N. Dattagupta, "Detection of Biotinylated Nucleic Acid Hybrids by Antibody–Coated Gold Colloid," Anal. Biochem. 171, 217–222 (1988).

A.H.N. Hopman, J. Wiegant, G.I. Tesser, and P. Van Dujin, "A Non–Radioactive In Situ Hybridization Method Based on Mercurated Nucleic Acid Probes and Sulfhydryl–Hapten Ligands," Nucleic Acids Res. 14, 6471–6488 (1986).

A. Oser, W.K. Roth, and G. Valet, "Sensitive Non–Radioactive Dot–Blot Hybridization Using DNA Probes Labeled with Chelate Group Substituted Psoralen and Quantitative Detection by Europium Ion Fluorescence," Nucleic Acids Res. 16, 1181–1196 (1988).

L.M. Smith, S. Fung, M.W. Hunkapiller, T.J. Hunkapiller, and L.E. Hood, "The Synthesis of Oligonucleotides Containing an Aliphatic Amino Group at the 5' Terminus: Synthesis of Fluorescent DNA Primers for Use in DNA Sequence Analysis," Nucleic Acids Res. 13, 2399–2412 (1985).

J. Wiegant, T. Ried, P.M. Nederlof, M. van der Ploeg, H.J. Tanke, and A.K. Raap, "In Situ Hybridization with Fluoresceinated DNA," Nucleic Acids Res. 19, 3237–3241 (1991).

L.E. Morrison, T.C. Halder, and L.M. Stols, "Solution–Phase Detection of Polynucleotides Using Interacting Fluorescent Labels and Competitive Hybridization," Anal. Biochem. 183, 231–244 (1989).

M. Ishikawa, K. Hirano, T. Hayakawa, S. Hosoi, and S. Brenner, "Single–Molecule Detection by Laser–Induced Fluorescence Technique," Jpn. J. Appl. Phys. 33, 1571–1576 (1994).

M. Eigen and R. Rigler, "Sorting Single Molecules: Application to Diagnostics and Evolutionary Biotechnology," Proc. Natl. Acad., U.S.A. 91, 5740–5747 (1994).

S. Nie, D.T. Chiu, and R.N. Zare, "Probing Individual Molecules with Confocal Fluorescence Microscopy," Science 266, 1018–1021 (1994).

* cited by examiner

METHOD FOR DETECTING POINT MUTATIONS IN DNA UTILIZING FLUORESCENCE ENERGY TRANSFER

This application claims the benefit of U.S. Provisional Application No. 60/029,775, filed Oct. 29, 1996.

This invention relates to the identification of genetic mutations and, more particularly, to a method of detecting point mutations in DNA utilizing fluorescence energy transfer. This invention was supported by National Institutes for Health grant DK36288 to the Center for Biotechnology, University of Nebraska-Lincoln.

BACKGROUND

The detection of mutations in sequences of DNA is becoming increasingly important in medical science. The detection of such a mutation in a DNA sequence typically involves the use of an oligodeoxyribonucleotide probe that is complementary to the target DNA sequence. The probe is designed to present some moiety, such as a radioactive element, that signals the occurrence of hybridization in a filter assay or an electrophoretic gel. The identification of hybridization has been used diagnostically for specific bacterial infections by detection of *Mycobacterium tuberculosis* genomic DNA, gonorrhea rRNA, Chlamdia genomic and plasmid DNA and *Escherichia coli* and *Bacillus subtilus* rRNA. Hybridization assays have also been developed for viral detection, including cytomegalovirus (CMV), human papilloma virus (HPV), and HIV-1.

By combining target amplification with allele specific oligonucleotides, small samples of human DNA can be analyzed for puxposes of genetic screening, including the study of genetic changes associated with well-known inherited diseases. For instance, cancers typically display familial site-specific clustering. The identification of this kind of clustering can aid in the determination of enhanced risk for the development of the particular cancer. In addition, hereditary metabolic variations in DNA have been identified that affect the metabolism of known carcinogens. A variation that would increase the metabolism of a carcinogen may impact the likelihood of the development of cancer and, if developed, the speed of the cancer's growth.

Traditional hybridization methods have been developed which employ radioactive probes with separation on filters. While radioactive probes have performed suitably well, growing concern over the use of radioactive materials has stimulated a search for alternative probes that achieve similar levels of sensitivity and performance without the risks and dangers associated with radioactive materials. For instance, biotin has been incorporated into an oligodeoxyribonucleotide for use in biotinavidin-linked analyses. In addition, numerous modifications of DNA have been used in the development of other alternative probes, including links to antibodies, gold-antibodies, mercury for double antibody reactions, eupsoralen, and fluorescent dye links for fluorescence detection of hybridization. These alternative methods typically allow approximately $10^5$ to $10^6$ copies of the DNA to be detected.

These and related advancements in the art have given rise to several methods of DNA mutation detection. These methods include denaturing gradient gel electrophoresis (DGGE), single-strand conformational polymorphisms (SSCP), temperature gradient gel electrophoresis (TGGE), the heteroduplex method (HET), ribonuclease cleavage, chemical cleavage of mismatch (CCU), ligase assay, allele-specific amplification (ASA) dideoxy fingerprinting (ddF), and allele-specific oligonucleotides (ASO). DGGE, SSCP, TGGE, HET, and ddF are frequently used to locate which exons of a gene contain mutations.

The currently available non-radioactive methods for detecting mutations in DNA have been somewhat problematic. For example, these methods have been generally unable to consistently provide accurate results in detecting point mutations in DNA. These detection methods have also proven to be time-consuming and quite costly to use. In addition, these non-radioactive mechanisms require a significant amount of DNA to perform their detecting function, though many times only a small quantity of DNA is available for analysis. Moreover, these methods are difficult to use, often requiring complex instruments and highly trained technicians not available in many laboratories. Finally, the materials utilized in these methods are generally either fragile or prone to degradation during the testing procedure.

SUMMARY OF THE INVENTION

It is, therefore, a primary object of the present invention to provide a method for quickly and accurately detecting point mutations in DNA.

It is also an object of the present invention to provide a method for quickly and accurately detecting point mutations in DNA that does not utilize radioactive material.

It is a further object of the present invention to provide a method for quickly and accurately detecting point mutations in DNA that requires only a relatively small amount of DNA to perform its detection finction.

It is another object of the present invention to provide a method for quickly and accurately detecting point mutations in DNA that is inexpensive, non-complex and easy to use.

It is yet another object of the present invention to provide a method for quickly and accurately detecting point mutations in DNA that is durable and less likely to experience degradation of its constituent components during the testing procedure.

It is yet another object of the present invention to provide a method for deteting point mutations in DNA which requires minimal sample preparation.

To accomplish these and related objectives, the present invention relates to a method for detecting point mutations in DNA using a fluorescently labeled oligomeric probe and fluorescence resonance energy transfer (FRET). The selected probe is labeled at each end with a fluorescent dye, which act together as a donor/acceptor pair for FRET. The fluorescence emission from the dyes changes dramatically from a probe/target duplex stage, wherein the probe is hybridized to the complementary strand of target DNA, to the single strand stage, when the probe is melted to become detached from the target DNA. The change in fluorescence is caused by the dyes coming into closer proximity after melting occurs and the probe becomes detached from the target DNA strand. The change in fluorescence emission as a function of temperature is used to calculate the melting temperature of the complex or $T_m$. Where there is a base mismatch between the probe and the target DNA strand, indicating a point mutation in the target DNA strand, the $T_m$ has been found to be significantly lower than the $T_m$ for a perfectly match probe/target duplex. The present invention allows for the detection of the $T_m$, which allows for the quick and accurate detection of a point mutation in the target DNA strand.

DESCRIPTION OF THE PREFERRED EMBODIMENT

Figure 1:
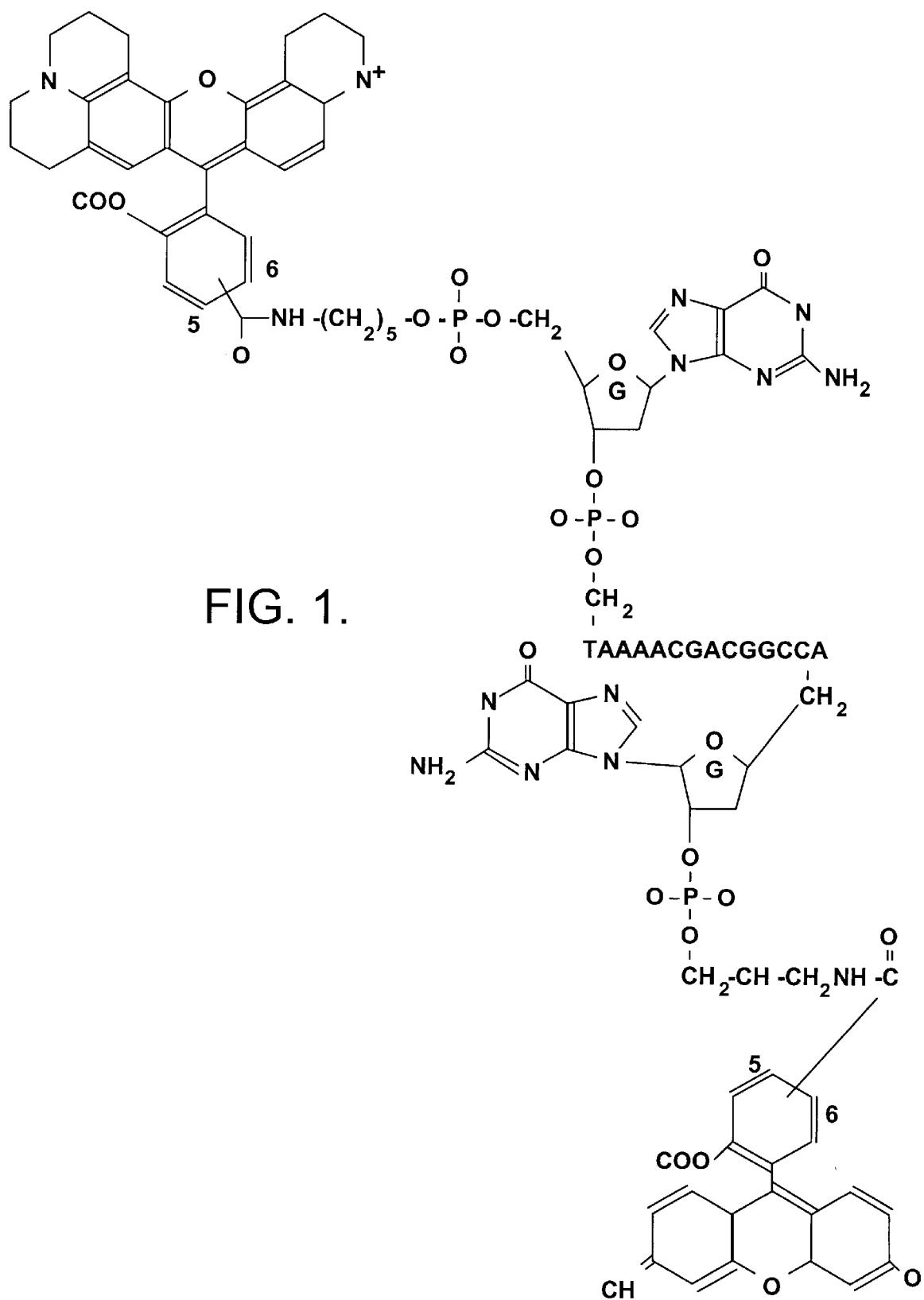
FIG. 1 illustrates the structure of a representative 16-base oligomer probe for use in connection with the method of the present invention. The probe includes x-rhodamine attached to the 5' end of the probe and fluorescein attached to the 3' end, which act as a acceptor and donor, respectively, for FRET.

The method of the present invention is carried out utilizing a probe, which is typically a deoxyribonucleotide oligomer. An illustrative 16-base probe is shown in FIG. 1. The base length and specific nucleotide sequence of the probe will, of course, vary depending on the target sequence of the DNA strand. A probe having a length of 10 to 30 bases have been found to work suitably well. The probe length must be sufficient for essentially full hybridization so an accurate melting transition can be detected even for the mismatch. It is understood that the precise sequence of the probe may be altered or engineered to complementarily match the target DNA strand to be assayed and, consequently, all such sequences are within the scope of the present invention. The probe can be used in a solution or on a solid-phase support, depending on the application.

The probe of the present invention must be fluorescently labeled. A pair of dyes are covalently linked to the probe as labeling agents. The dyes act as a donor/acceptor pair for FRET. The efficiency of the energy transfer from the donor dye to the acceptor dye is sensitive to distance, the efficiency rising dramatically as the distance between the probes is decreased. When the probe is attached to the target DNA sequence, the dyes are relatively spaced apart, thereby inhibiting efficient transfer of energy between the dyes. When the probe becomes detached from the DNA, the dyes come into closer proximity. The energy transfer between the dyes rises, which is indicative of the melting of the duplex.

A number of considerations are involved in choosing a donor/acceptor dye pair and in designing the probe. The dyes should have a high molar absorptivity and quantum yield, and the fluorescence lifetime of the donor should be sufficiently long to ensure accurate measurement. The emission of the dyes should have limited sensitivity to factors other than changes in distance. For instance, the probe should be resistant to changes in pH, ion concentration and to photobleaching. Another important consideration is the value of $R_0$ (the distance at which FRET is 50% efficient), relative to the length of the oligomer. The value of $R_0$ must therefore be calculated or at least estimated. This value derives from the overlap of the emission band of the donor dye with the absorption band of the acceptor dye, and also from the region of the wavelength range on which the overlap integral is centered. Further, the dyes must be attached to the oligomer with sufficient freedom of rotation so that the average value of the orientation factor $K^2$, will be close to two-thirds. With these considerations taken into account, numerous successful probes have been designed ranging from 14–20 bases and with the following donor/acceptor pairs: fluorescein/tetramethylrhodamine, fluoresceinix-rhodamine, and fluorescein/Cy-3. In all of these probes, the linker arms between the oligomer and the dyes were either 3- or 6-carbon chains. It is to be understood, however, that other probes and donor/acceptor pairs may be developed in accordance with this invention and are, thus, within its scope.

The difference in the fluorescence emission of the probe as a single strand or in a duplex structure derives from a difference in an excitonic inteaction in the weak-coupling limit, an interaction that varies with the inverse sixth power of the distance between transition moment dipoles of the donor and acceptor dyes or moeties. The steady-state fluorescence emission intensity of either dye is proportional to its quantum yield, which, neglecting static quenching, is the ratio of the rate constant for fluorescence ($k_F$), which derives from the Einstein B coefficient, to the sum of the microscopic rate constants that deactivate the state from which the fluorescence arises, which is assumed to be the lowest singlet ($S_1$). These processes can be summed as follows: $k_F + k_I + k_I$; where $k_I$ is the sum of all nonfluorescence processes that deactivate $S_1$ in the absence of acceptor, and $k_t$ is the rate constant for resonance energy transfer. The quantum yield of donor fluorescence in the presence of acceptor is then:

$$\Phi_r = k_F/(k_F + k_I + k_t) = k_F/[k_F + k_I)(1 + X^6)]$$
$$= \Phi_O/(1+X^6),$$

where $\Phi_O$ is the quantum yield in the absence of transfer or, in other words, the absence of acceptor. The quantity X is $R_0/R$, where R is the distance between the donor and acceptor, and $R_0$ is the donor/acceptor distance at which the rate constant for tnsfer equals $k_F + k_I$. $R_0$ can be calculated relatively easily by one skilled in the art from the measured spectroscopic properties of the donor and acceptor and applying the assumptions with respect to the effective refractive index of the medium separating the donor and acceptor and the rotational averaging of the angular portion of the dipole-dipole interaction. It is assumed that $R_0$ for fluorescing x-rhodamine (60 Å) remains constant throughout the melting process and, therefore, changes in the steady-state intensity, which are proportional to $\Phi_r$, derive from changes in R.

The donor and acceptor dyes may be attached to the probe at any two points. It is preferred that the dyes be spaced relatively far apart on the probe. Most preferably, the dyes are attached at opposite ends of the probe. Because the FRET donor and acceptor are preferably relatively far apart, FRET is minimized ($k_t$ is low) for a probe/target DNA duplex. When the dyes are spaced apart, the donor emission is high and acceptor emission is low. This is illustrated by the solid line in FIG. 2. Upon melting to two single strands, the duplex structure is lost and more flexible single strand brings the donor and acceptor closer together. Consequently, FRET is significantly increased, and donor emission decreases and acceptor emission increases. This is shown by the broken line in FIG. 2. The melting temperature, $T_m$, is the temperature at which the fraction (f) of the total probe bound to complement is 0.5. In another embodiment, the FRET acceptor acts as a quencher without having its own fluorescence emission.

The melting process is a sufficiently sharp transition that it may be treated as a two-state process. This can be expressed mathematically by considering B to be the equilibrium concentration of B DNA, and $C_T$ and $P_T$, respectively, to be the total target and probe concentratons. The equilibrium constant for helix formation is then $K=B/[(C_T-B)(C_P-B)]$ and $f=B/P_T$, with all concentrations referenced to a standard state of 1 M. The equilibrium constant for $C_T>P_T$ can then be written as follows:

$$K=[f/(1-f)][P_T(1-f)+(C_T-P_T)]^{-1},$$

Φwith $[f(1-f)]=1$ at $T_m$.

At $T_m$, $\Delta G=0$, and $$\Delta G°=-(RT_m)\ln(K),$$

where R is the molar gas constant. If values of $\Delta H°$ and $\Delta S°$ are available for the given solvent conditions and assumed to be independent of temperature up to $T_m$ then, since $\Delta G°=\Delta H°-T_m\Delta S°$, $T_m$ can be calculated from this formula:

$$T_m=\Delta H°/[\Delta S-R\ln(K)],$$

This calculation is dependent upon probe and target concentrations through K, and the steepness of the transition at the midpoint, $\partial f/\partial T$, gives $\Delta H°$ at $T_m$ for a true two-state process, and it can be shown that $$\Delta H°=RT^2_m(\partial f/\partial T)[4+1/(C_T/P_T-1/2)].$$

Alternatively, $T_m$ can be predicted from empirical equations.

The $\Delta T_m$ for a DNA sequence due to a point mutation or base-pair mismatch has been found to be from about 2 degrees to about 12.5° C. as compared to a perfect probe/target match. The $\Delta T_m$ has been found to be dependent on the length of the probe/DNA strand duplex and also upon the location of the point mutation or base-pair mismatch in the duplex. For instance, if the point mutation lies toward either end of the duplex, $\Delta T_m$ will generally be lower, typically in the range of about 6 to about 8° C. If the point mutation or base-pair mismatch resides toward the center of the duplex, $\Delta T_m$ will be relatively higher, typically in the range of about 9 to about 11° C., it has been found that $\Delta T_m$ is generally equivalent to about 1 to about 1.5° C. per percent base mismatch in the oligomer probe. It is to be appreciated that $\Delta T_m$ will vary depending on not only the length of the duplex and location of mutation, but also will vary depending on the specific order of the sequence. Consequently, all such variances are within the scope of the disclosure.

EXAMPLE

The following example illustrates the performance of the method of the present invention. The example should be construed only as illustrative and not in limiting sense.

For purposes of this example, a 16-base deoxyribonucleotide oligomer with x-rhodmine covalently bound to the 5' end and fluorescein to the 3' end will be discussed. This probe is shown in FIG. 1 and will be addressed as R*16*F. As seen in FIG. 1, the R*16*F probe comprises x-rhodamine-5'-GTAAAACGACGGCCAG-3'-fluorescein. The R*16*F probe was designed to be complementary to bases 6291 to 6306 of the 7249-base phage DNA M13mp18 (+), one base removed from the restriction site. Hybridization of the R* 16*F to a complementary strand results in a B DNA helical structure with the 3'-fluorescein and the 5'-x-rhodamine positioned at opposite ends.

The R*16*F probe was selected with several considerations in mind. First, the length of the probe is sufficient for the melting temperature of the duplex to be above room temperature, ensuring complete hybridization at 25° C. Second, for Förster energy transfer to reflect small changes in interdye distances, the average distance apart should be near $R_0$. The average distance in the duplex would be approximately 10% greater than $R_0$. Finally, the placement of dyes on bases 1 and 16 results in their being located 180 degrees apart when viewed down the helix axis, enhancing their separation and the signal change associated with melting.

A steady-state fluorimeter with computerized data acquisition (Photon Technology International, Inc., Model A-1010) was modified to use as excitation light the 488-nm line of a Coherent Innova 70-4 Ar⁺ laser. A controllable shutter between the excitation beam and the cuvette was utilized to ensure that the solution was exposed to excitation light only during the course of a scan, to minimize the photobleaching of fluorescein. The R*16*F probe was obtained from Research Genetics in Huntsville, Ala. The perfect (CTGGCCGTCGTTTTAC) and single mismatch (CTGGCCGTTGTTTTAC) complements were synthesized by the inventors, and the M13mp18(+) was from obtained Sigma in St. Louis, Mo.

The buffer was 0.01 M NaPi, pH 8, 1 mM EDTA and 0.18 M NaCl, with a total volume of 250 µl in a stoppered microcuvette. Stock solutions of R*16*F and its complement were diluted to 10 and 20 nM, respectively, and allowed to hybridize for 45 minutes, essentially to completion. The duplex with the mismatch was monitored spectroscopically for the last 15 minutes of the procedure to ensure that no further change occurred.

For the R*16*F/M13 duplex, stock solutions were diluted to 6.6 and 13.2 nM, respectively, and the solution left for 2.5 minutes in a heat block (Thermodyne, model 17600) at 65° C. Hybridization occurred as the solution returned slowly to 20° C. over 1 hour. The cuvette was capped prior to data collection to prevent evaporation at high temperatures. Scans were collected from 502 to 625 nm every 3 to 4° C., from 16 to 74.5° C., 16 to 67° C., and 20 to 76° C. for the R*16*F duplex, mismatch duplex, and M13 duplex, respectively. The solutions were equilibrated for 10 minutes at each temperature prior to scanning.

The temperature of the solution was controlled using flow through the cuvette holder from a Lauda K-2/R constant-temperature circulating bath. The temperature of the circulating water for each scan was noted. After the experiment, a thermistor was placed in the buffer-filled cuvette to obtain the actual solution temperature for each temperature noted previously. Baseline scans, which included the 583nm Raman scattering from water and background introduced with the M13, were collected prior to each data set and subtracted from all subsequent scans prior to analysis.

The emission scan of the R*16*F contained two peaks: The peak at 520 nm was derived from direct absorption by fluorescein of the 488-nm excitation light, modified by FRET. The peak at 610 nm was due primarily to FRET from the fluorescein to the x-rhodamine, with a small contribution from direct absorbance by x-rhodamine of the excitation light. In the perferred embodiment, the fraction, $f$, of R*16*F proble hybridized to its complement target DNA is represented in the following equation:

$$f=\delta(Y)/[1-Y(1-\delta)],$$

where $$\delta=I^U_{rhod}/I^H_{rhod}$$

and $$Y=(<p>-p^U)/(p^H-p^U),$$

and $I_{rhod}$ is the peak rhodamine emission intensity, p is the ratio of the 520 to 610 nm peaks, <p> is any observed intermediate value of p, and the superscripts U and H refer, respectively, to unhybridized and hybridized R*16*F. The fraction of bound R*16*F was calculated at each temperature measured, and was used to construct the melting curves. The sets of data points on each plot that correspond to the premelting and postmelting regions and to the melting process were each fit by linear regression and the $T_m$ taken as the mid-point of the transition region.

In another embodiment, a fraction of the probe hybridized to target DNA is determined by analyzing the donor emission intensity in unhybridized and hybridized states. This embodiment enables a non-fluorescent quencher to be used as the accepted dye, although it does not require that the acceptor be non-fluorescent.

Figure 2:
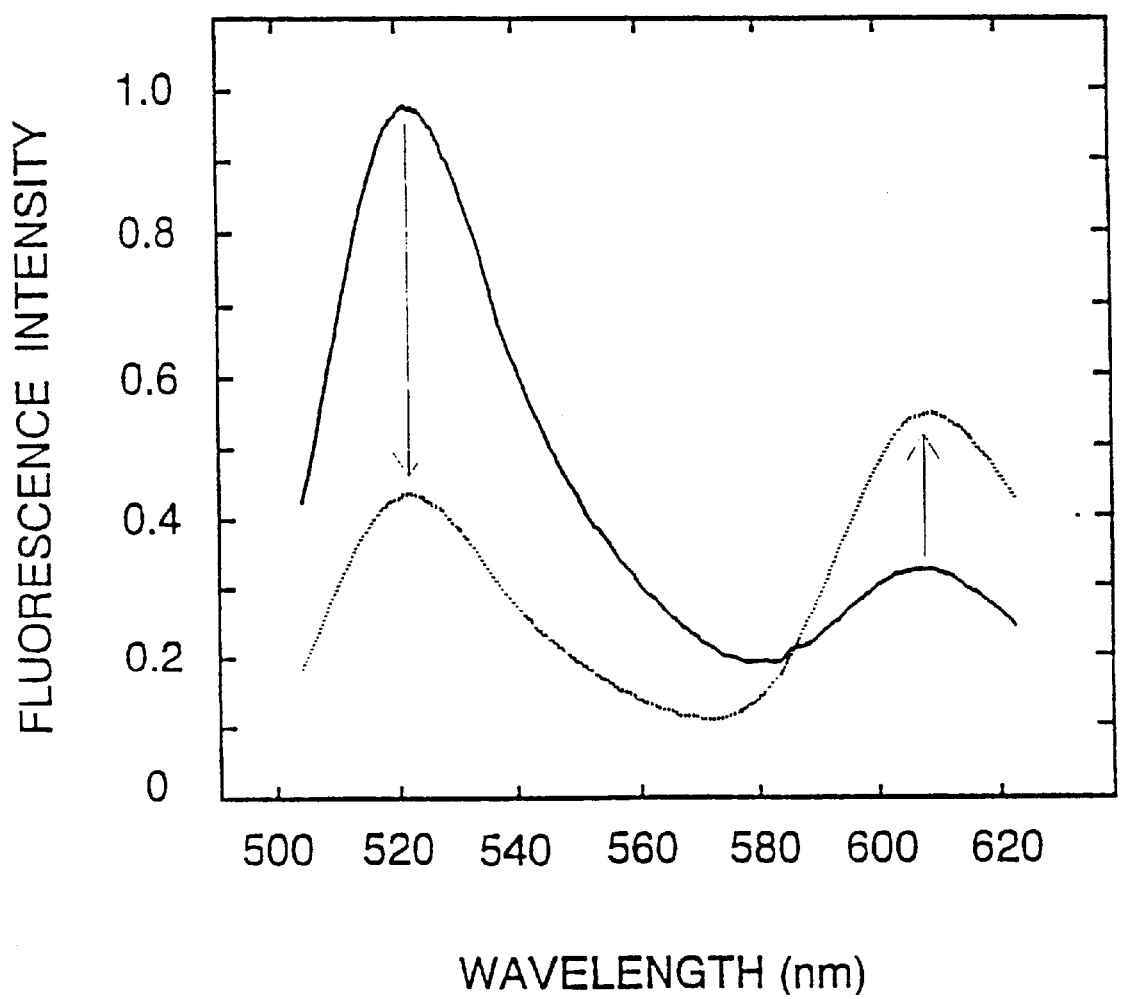
FIG. 2 is a graph plotting fluorescence intensity versus wavelength and showing steady-state fluorescence emission scans for the probe of FIG. 1 as a hybridized duplex structure with its complementary target DNA strand in the solid curve, and as a single strand upon melting in the broken curve.
Figure 3:
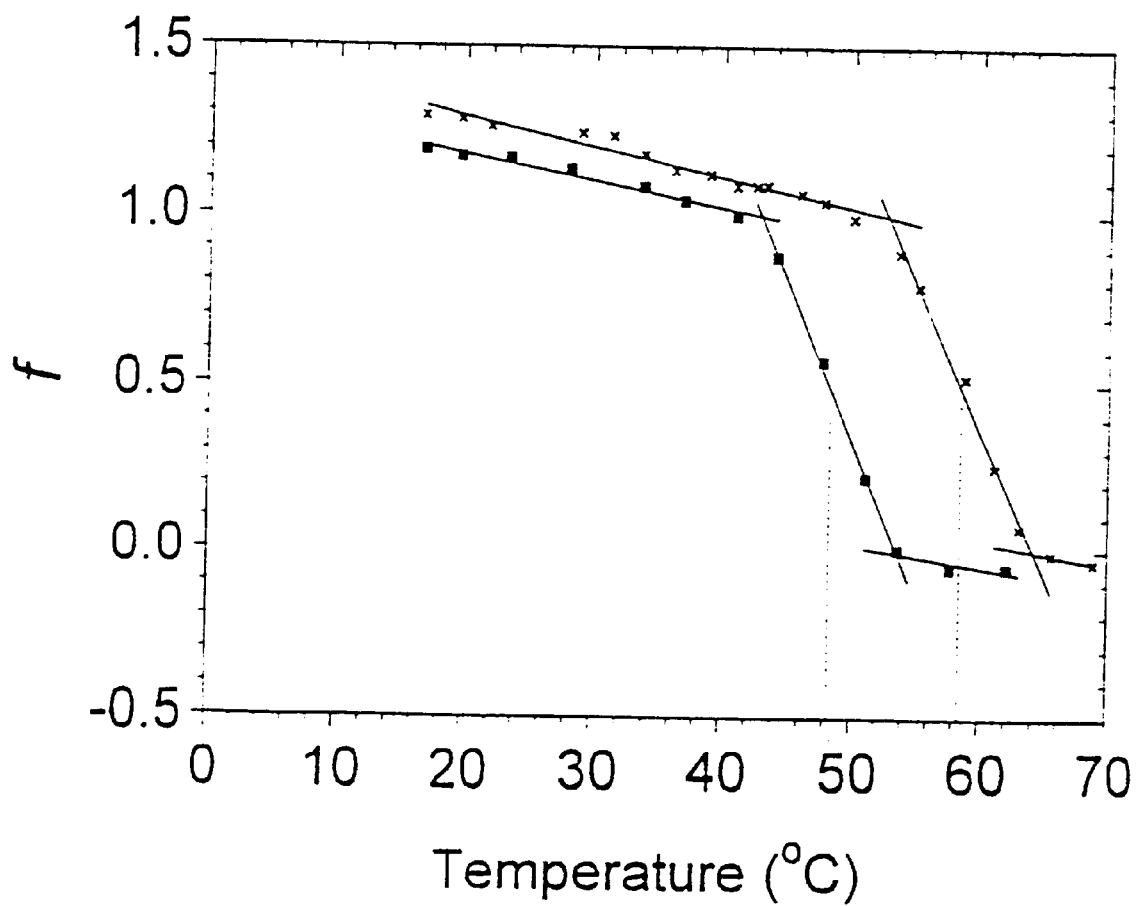
FIG. 3 is a graph plotting the fraction of probe hybridized to target DNA versus temperature and showing melting curves for a perfectly matched duplex of the probe of FIG. 1 and its complementary target DNA strand, and the probe of FIG. 1 with its complementary target DNA strand having a single central base substitution, the vertical broken lines indicating the melting point for each respective curve.
Figure 4:
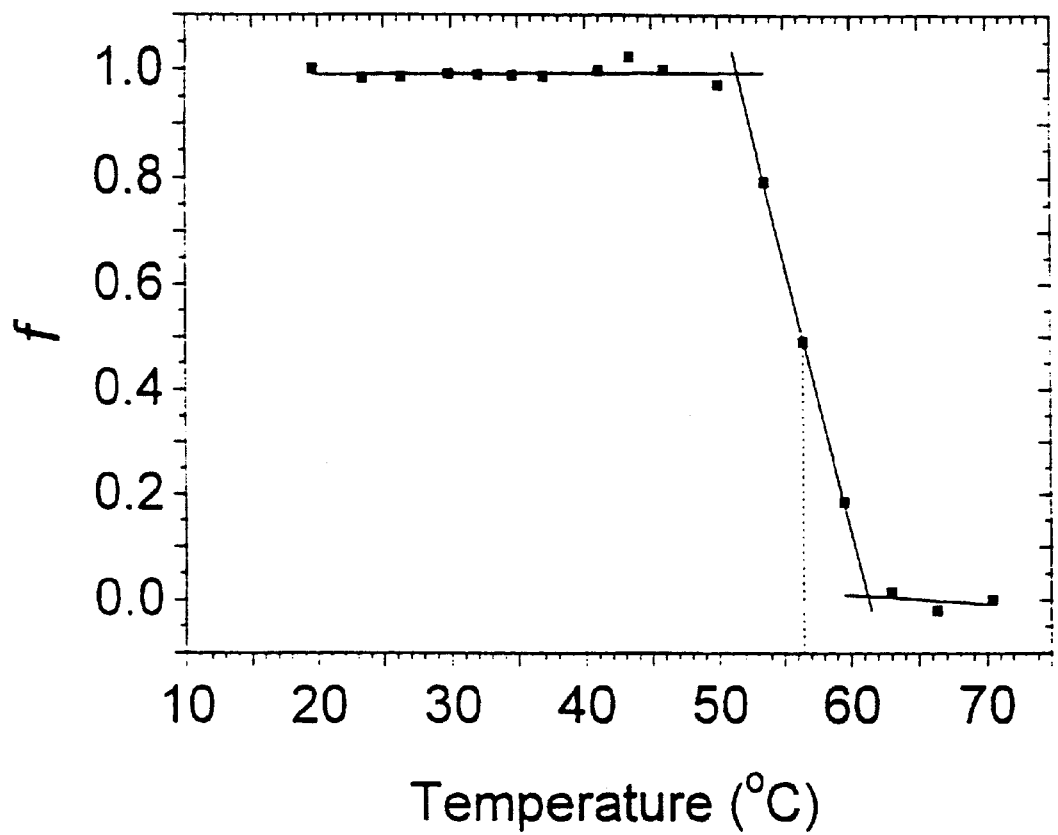
FIG. 4 is a graph plotting the fraction of probe hybridized to target DNA versus temperature and showing the melting curve for a duplex including the probe of FIG. 1 bound to a 7249-base phage target DNA, M13mp18+, which contains a 16base complementary sequence, the vertical broken line indicating the melting point of the duplex.

The fluorescence emission scans of R*16*F differ dramatically for the duplexed and single-strand forms, as discussed above in FIG. 2. Melting results in a decrease in the fluorescence emission of the fluorescein and an increase in the rhodamine emission, which is the result of the decrease in the inter-dye distance. FIG. 3 illustrates melting curves for the duplexes formed by R*16*F hybridized to the perfect 16-base complement and to the 16-base complement with a single C→T base substitution. The $T_m$s for these duplexes are 58.3 and 48.2° C., respectively. FIG. 4 shows the melting curve for the duplex formed between R*16*F and its target sequence in M13mp18(+), with a $T_m$ of 56.4° C. The mismatch is easily detected and gives rise to a $\Delta T_m$ of 10° C.

The $T_m$ of the perfect complement can be predicted rather well from this empirical relationship:

$$T_m(°C.)=81.5+16.6(\log_{10}[Na+])+0.41(\%G+C)-600/N,$$

where N is the number of bases in the shorter oligo strand. For the R*16*F probe, the predicted $T_m$ of 55.5° C. is consistent with the observed values of 56.4 and 58.3° C. for M13 and the 16-mer complement, respectively.

$T_m$ is expected to be insensitive to secondary or higher structures around the probe site which are known by kinetic studies to characterize M13mp18(+). A comparison of FIGS. 3 and 4 shows that $T_m$ is, in fact, nearly insensitive to the length of the target DNA, particularly considering that the target and probe concentrations are lower for the M13. Assuming that the standard state enthalpy and entropy changes are the same for the two duplexes, a lower $T_m$ may be predicted for the M13 by about 0.9 degrees. It is not known whether the remaining 1-degree difference is insignificant or reflects a perturbation of the target structure. More involved calculations of the melting temperature can be made in which nearest-neighbor interactions are included in $\Delta H°$ and $\Delta S°$. However, these quantities are not available for the above buffer conditions, and the above empirical relationship provides a sufficiently close estimate of $T_m$ for the purpose of experimental design.

The following thermodynamic quantities for the probe hybridized to the 16-base complement were calculated: $\Delta G°=-49.6$ kj/mole, $\Delta H°=-373\pm21$ kJ/mole of duplex (−23.3 kJ/mole of base pair) and $\Delta S°=-977\pm17$ J/mole-K at $T_m=331.5$ K. Using values from Breslauer et al. for the disruption of a CG base pair adjacent to a CG base pair ($\Delta H°$ and $\Delta S°$ more positive by about 50 kJ/mole and 116 J/mole-K), a $T_m$ of 320.1 K for the mismatched duplex can be calculated. This is a decrease in $T_m$ of 11.4° C., which is in agreement with the 10.1° C. decrease observed. In this calculation, the changes in $\Delta H°$ and $\Delta S°$ for lowering [Na+] from 1 M to 0.2 M have been neglected.

It is convenient to have measurable fluorescence for both the double-labeled oligo as a single strand and in the duplex, as well as sensitivity of the fluorescence to changes in the donor/acceptor distance. If $\theta$ as the ratio of the quantum yield in the presence of the acceptor to that in the absence, then $\theta=(1+X^6)^{-1}=1-\eta$, where $\eta$ is the efficiency of transfer. It is straightforward to show that the maximum sensitivity of $\theta$, where sensitivity is defined as $-d\theta/dX$, to a change in R occurs at $R=R^*=(0.946)R_0$, for which $-d\theta/dX-1.54$. For $R=R_0$, $-d\theta/dX=1.5$, and for either $R^*$ or $R_0$, a 1% change in fluorescence intensity corresponds to a change of 0.6 Å in R for $R_0=60$ Å. The sensitivity decreases in 1 on either side of $R_0$ (at $R=1.344 R_0$ and at $R=0.847 R_0$) where the respective values of $\theta$ are 0.855 and 0.269, a normalized change from 1 to 0.32. For the 16-base oligomer, distance changes on melting correspond to $R=1.142 R_0$, decreasing to $R=0.858 R_0$, and the change in normalized fluorescence intensity for the donor, as in FIG. 2, is from 1 to 0.44. These distance considerations are linked to the desired $\Delta T_m$, which increases as the length of the probe decreases and is maximized for location of the mismatch at or near the center of the probe.

Both optical and calorimetric measurements of the melting transition agree for a 10-mer duplex having GC base pairs on the ends, showing that the process can be treated to high precision as a two-state process. Intermediates have been detected for single strand melting, however, and there may be instances where bases, particularly at the ends of the duplex, are unpaired before full strand separation. On the other hand, the large change in fluorescence emission reported here would be expected only after actual strand separation and, thus, might be expected to lead to the appearance of a sharper transition than that observed by absorbance. Monitoring absorbance changes associated with melting is not feasible for duplexes between short oligomers and long strands of DNA due to the overwhelming background from the long strand.

The long DNA strand tested in this example was single-stranded. Special hybridization techniques are required with DNA that is originally duplex. The melting process, once the probe has bound, should closely resemble that of the example. It is essentially independent of higher order structure in the vicinity of the target, owing to the large $\Delta H°$ of melting. In practice, one would titrate the probe with DNA to determine the number of copies of the target, and then carry out the melting experiments as described above. Once hybridization is achieved and having an estimate of $T_m$ from the foregoing equations, one could start the temperature ramp about 10 degrees below the expected $T_m$ for the mismatch and complete the analysis within 1 hour.

The sharp transition detected by FRET using the double-labeled oligonucleotide allows a rapid and clear determination of whether a mismatch is present in the target. The quickness and accuracy of this method are not found in methods and procedures currently available in the art. Further, the method of the present invention is straightforward with few steps to follow. A technician will be able to carry out this method quite easily with little traing and, thus, the method is economical and efficient. The materials used in this method are hearty and unlikely to degrade or break during the procedure. This will reduce the need to repeatedly perform the testing due to failure of the components. In addition, only a small amount of DNA is needed to make a point mutation determination utilizing this method. The ultimate beneficiary of the method of the present invention will be the patient, who will obtain resuts quickly and inexpensively and who will be able ito rely upon the accuracy and reliability of the results of the test.

It is, therefore, readily apparent that this invention is capable of attaining the objects set forth above as well as other advantages that are obvious and inherent to the invention. It is to be understood that other subcombinations are of utility and may be employed without reference to other features and combinations of the invention. Because many embodiments may be made of the invention without departing from the scope of this disclosure, it is to be understood that all matter set forth herein is to be interpreted as illustrative only.

What is claimed is:

1. A method for detecting point mutations in a selected target DNA sequence, wherein the sequence has a reference melting point at which it becomes detached from a complementary sequence, the method comprising:

providing a probe having a sequence complementary to the target DNA sequence;

attaching at least two dyes to the probe, the dyes producing FRET emissions, wherein the FRET emissions change in response to a change in proximity of the dyes to each other, allowing the probe to hybridize with the DNA sequence to form a probe/target DNA duplex;

recording an attached value of the FRET emissions from the dyes of the probe/DNA duplex;

heating the probe/DNA duplex;

monitoring the temperature at which the FRET emissions from the probe and duplex are reduced to a detached value as a result of the change in the proximity of the dyes to each other; and determining an observed melting point of the probe/target DNA duplex by recording the temperature of the probe/DNA duplex at the midpoint between the attached value of the FRET emissions and the detached value of the FRET emissions;

whereby if the observed melting point is lower than the reference melting point at least one point mutation exists.

2. The method of claim 1 wherein the dyes are attached to opposite ends of the probe.

3. The method of claim 2 whereby a point mutation exists if the observed melting point is about 2° to about 12.5° C. lower than the reference melting point.

4. The method of claim 3 whereby a point mutation exists if the observed melting point is about 6 to about 11° C. lower than the reference melting point.

5. The method of claim 1 wherein the probe is an oligodeoxyribonucleotide.

6. The method of claim 5 wherein the probe is a oligomer having a length of 10 to 30 bases.

7. A method for detecting the location of a point mutation in a selected target DNA sequence, wherein the sequence has a reference melting point at which it becomes detached from a perfectly matched complementary sequence, the method comprising:

providing a probe having a base sequence complementary to the target DNA sequence;

attaching two fluorescent dyes to the probe, the dyes acting together as a donor/acceptor pair for FRET and producing FRET emissions;

allowing the probe to hybridize with the DNA sequence to form a probe/DNA duplex;

recording an attached value of the FRET emissions from the dyes of the probe/DNA duplex;

heating the probe/DNA duplex;

monitoring the temperature at which the FRET emissions from the probe/DNA duplex are reduced to a detached value; and determining an actual melting point of the probe/DNA duplex by recording the temperature of the probe/DNA duplex at the midpoint between the attached value of the FRET emissions and the detached value of the FRET emissions;

whereby if the actual melting point is about 9 to about 11° C. lower than the reference melting point, the point mutation is located near the center of the target DNA sequence, and whereby if the actual melting point is about 6 to about 9° C. lower than the reference melting point, the point mutation is not located near the center of the target DNA sequence.

8. The method of claim 7 wherein the dyes are attached to opposite ends of the probe.

9. The method of claim 8 wherein the probe is an oligodeoxyribonucleotide.

10. The method of claim 9 wherein the probe is a oligomer having a length of 10 to 30 bases.

11. The method of claim 10 wherein the probe is a 16-base oligomer.

12. A method for detecting point mutations in a selected target DNA sequence, wherein the sequence has a reference melting point at which it becomes detached from a complementary sequence, the method comprising:

providing a probe having a base sequence complementary to the target DNA sequence;

attaching at least two labels to the probe, the labels acting together to produce a visually observable event when the distance between the labels changes;

allowing the probe to hybridize with the DNA sequence to form a probe/target DNA duplex;

heating the probe/DNA duplex; and determining an observed melting point of the probe/target DNA duplex by recording the temperature of the probe/DNA duplex when the event is observed;

whereby if the observed melting point is lower than the reference melting point at least one point mutation exists.

13. The method of claim 12 wherein the labels are attached to opposite ends of the probe.

14. The method of claim 13 whereby a point mutation exists if the observed melting point is about 2° to about 12.5° C. lower than the reference melting point.

15. The method of claim 14 whereby a point mutation exists if the observed melting point is about 6 to about 11° C. lower than the reference melting point.

16. The method of claim 12 wherein the probe is an oligodeoxyribonucleotide.

17. The method of claim 16 wherein the probe is a oligomer having a length of 10 to 30 bases.

* * * * *

UNITED STATES PATENT AND TRADEMARK OFFICE
CERTIFICATE OF CORRECTION

PATENT NO. : 6,248,518 B1
DATED : June 19, 2001
INVENTOR(S) : Lawrence J. Parkhurst, Kay M. Parkhurst and Lyle Middendorf It is certified that error appears in the above-identified patent and that said Letters Patent is hereby corrected as shown below:

<u>Title page,</u>
Item [22], the filing date should be -- October 28, 1997 --

Signed and Sealed this

Eighth Day of June, 2004

JON W. DUDAS
*Acting Director of the United States Patent and Trademark Office*